United States Patent [19]

Lundblad et al.

[11] 4,412,990

[45] Nov. 1, 1983

[54] COMPOSITION HAVING ENHANCED OPSONIC ACTIVITY

[75] Inventors: John L. Lundblad, El Cerrito; Miriam D. Budinger, Berkeley; Richard S. Schwartz, Burlingame, all of Calif.

[73] Assignee: Cutter Laboratories, Inc., Berkeley, Calif.

[21] Appl. No.: 394,977

[22] Filed: Jul. 2, 1982

[51] Int. Cl.³ ............ A61K 37/00; A61K 35/14
[52] U.S. Cl. ................................. 424/177; 424/101
[58] Field of Search ................... 424/177, 101

[56] References Cited

PUBLICATIONS

Biol. Abstr. vol. 66, (1978), 526.
Biol. Abstr. vol. 69, (1980), 51789.

Primary Examiner—Delbert R. Phillips
Attorney, Agent, or Firm—Theodore J. Leitereg

[57] ABSTRACT

There is disclosed a pharmaceutical composition for therapeutic use comprising an immune globulin and fibronectin in amounts sufficient to produce an opsonic activity in the composition that is greater than the additive opsonic activity of the individual agents or in amounts sufficient to produce a phagocytosis of infectious agents greater than the additive effect from fibronectin and immune globulin alone.

22 Claims, 1 Drawing Figure

COMPOSITION HAVING ENHANCED OPSONIC ACTIVITY

BACKGROUND OF THE INVENTION

1. Field of the Inventin

This invention relates to and has among its objects the provision of novel compositions for therapeutic use. Further objects of the invention will be evident from the following description wherein parts and percentages are by weight unless otherwise specified.

2. Description of the Prior Art

Fibronectin or cold insoluble globulin has been the subject of several recent reviews, editorials and clinical studies (Mossesson, et al, Blood, 56, 145-158, 1980; Saba et al, Amer. J. Med., 68, 577-594, 1980; Grause, J.A.M.A., 244, 173, 1980; Robbins et al, The Amer. Surg., 663-673, December 1980; Scoville et al, Ann. Surg., 188, 521-528, 1979). This substance, which is produced by a variety of cells including endothelial cells, epithelial cells and peritoneal macrophages is probably critical as a major component of the intracellular matrix. Circulating fibronectin is a glycoprotein molecule having a molecular weight of approximately 450,000 and is made up of two chains of approximately equal size linked by disulfide bonds (Mossesson et al, ibid.). Fibronectin is felt to be important in mediating cell to cell adhesion, cell to substrate anchoring and spreading, regulating cell locomotion, mediating attachment of fibrinogen and macrophages to collagen and acting as an opsonin or attachment factor for certain particles (above references). Severe trauma or major burns result in a decrease in plasma fibronectin and a concomitant opsonic defect which can be corrected by infusion of cryoprecipitate containing fibronectin (Robbins et al, ibid. and Scoville et al, ibid.). Such therapy has resulted in a marked improvement in cardiopulmonary function, correction of shock and normalization of other hematologic parameters suggesting an important role for fibronectin in organ and microvascular integrity (Scoville et al, ibid.).

The term reticuloendothelial system (RES) is used to refer to a system of mononuclear cells, scattered throughout the body, but with the common ability to engulf (phagocytize) blood-borne particulate matter. These cells, all derived from circulating monocytes, are found throughout many organ systems, but are especially concentrated as fixed tissue cellular elements in the spleen, lymph nodes, liver, and spleen. The RES functions as one of the body's primary host defense mechanisms for clearing and detoxifying the blood of particulate matter, including fibrin, fibrin monomers, endotoxin, platelet aggregates, damaged cellular elements, bacteria, viruses, and antibody-antigen complexes. Failure of this important host defense system leads to retention of potentially harmful particulates in the blood which may result in increased vascular permeability and edema or microvascular occlusion, both of which end in organ dysfunction.

Other functions ascribed to the RES include (1) antigen-antibody processing and interaction with lymphoid cells, a step required for normal antibody production and development of normal cellular immunity, (2) host defense against spontaneously arising tumors, (3) regulation of bone marrow hematopoiesis, (4) wound healing, and (5) remodeling of bone.

Depression of RES-mediated host defense mechanisms are seen in post-operative surgical patients, in patients who have sustained severe burns or trauma, in patients with bacterial infection, neoplasia, disseminated intravascular coagulation (DIC), and in other diseases of altered immunity. Such defects in host defense may result in sepsis and multiorgan failure. Failure in RES function is believed to result, in part, from a deficiency of plasma fibronectin which has been found to be depressed in these conditions. Fibronectin is also known to be involved in the process of wound healing.

Along with IgG, IgM, C3b and C5b fibronectin acts as an opsonin (attachment or ingestion factor) for a variety of different particles (opsonic activity). Initial assays for this opsonic activity involved the use of rat liver slices and radiolabeled gelatin coated liquid emulsion. Heparin was found to be a critical component in this system and prevention of alcohol denaturation of the fibronectin molecule by the addition of beta-mercaptoethanol was essential. Later, Molnar et al, Fed. Proc., 38, 303, 1979, using trypsin treated and untreated rat liver slices found that gelatin coated latex particles were bound to liver cells by fibronectin but were not ingested. Bevilacqua et al, J. Exp. Med., 153 42-60, 1981, subsequently found that fibronectin mediates attachment, but not ingestion, of gelatin coated red blood cells to human monocytes or peritoneal macrophages. For activity in this system, the fibronectin requires interaction with denatured collagen or gelatin and the presence of magnesium ions. Monocytes attached to a fibronectin-gelatin substrate bound four times as many red blood cells sensitized with IgG, IgM or C3b than did monocytes attached to a plastic surface. Such attached monocytes expressed an increased number of Fc and C3b receptors. Thus, while not promoting ingestion itself, fibronectin may augment Ig and C3b mediated internalization (Bevilacqua et al, ibid.).

Additional studies by Kuusela, Nature, 276, 718-720, 1978, indicate that labeled fibronectin binds strongly to *Staphylococcus aureus*. This effect was blocked by unlabeled fibronectin, plasma containing fibronectin, D-glucosamine, D-galactosamine, L-lysine, sodium chloride and urea. Divalent cations were not required for fibronectin binding to this organism. A subsequent report by Proctor et al, Clin. Res., 27, 650A, 1979, indicated that labeled fibronectin bound strongly to *S. aureus* and *Micrococcus luteus* but not *E. coli*. This was associated with enhanced *S. aureus* and M. luteus induced neutrophil chemiluminescence and bactericidal activity. Since these initial reports, two conflicting articles have appeared in the literature. One by Doran et al, Inf. and Immun., 33, 683-689, 1981, indicated that fibronectin probably binds to protein A on the surface of staphylococci since binding of labeled fibronectin was directly proportional to the cellular protein A content of several strains. Furthermore, binding was inhibited by the addition of soluble protein A (up to 50%). These data were in contrast, however, to those reported by Kuusela, ibid., and Verbrugh et al, *Inf. and Immun.*, 33, 811-819, 1981, who found no association between fibronectin binding and protein A content and could not inhibit binding with up to 100 micrograms/ml of this protein. This latter group also failed to demonstrate a significant role for fibronectin in promoting actual uptake of radiolabeled staphylococci by human polymorphonuclear leukocytes (PMNs) monocytes (MNs) or alveolar macrophages in the presence or absence of human serum containing antibody. It should be pointed out, however, that these latter studies were not designed to detect an effect of fibronectin on particle attachment. Thus, there is controversy about the actual role that fibronectin has in the host defense mechanism.

Proctor et al, Blood, 59, 681–687, 1982, have shown that fibronectin mediated the attachment of *S. aureus* to human PMNs but it did not promote PMN phagocytosis of bacteria.

SUMMARY OF THE INVENTION

It has been found that a composition comprising fibronectin and immune globulin has a synergistic effect on the opsonic or particle-phagocytic activity which is greater than that of either fibronectin or immune globulin alone. Consequently, the therapeutic capabilities and effectiveness of these two individual agents is significantly and synergistically enhanced when employed in the present composition. Therefore, the invention is a new combination product for use in immuno therapy. The preparation of the invention has application, for example, for prophylaxis and treatment of illness such as non-infectious and infectious diseases, in situations where there are either absolute or relative defects in in vivo opsonization, and in cases where abnormalities in the reticuloendothelial system are present.

One embodiment of the invention is a pharmaceutical composition for therapeutic use comprising an immune globulin and fibronectin in amounts sufficient to produce an opsonic activity of the composition that is greater than the additive opsonic activity of the individual agents alone or in amounts sufficient to produce phagocytosis greater than that mediated by fibronectin or immune globulin alone.

As an example, patients with severe burns have depressed levels of both fibronectin and immunoglobulin. The diminished fibronectin level leads to impaired RES function, and the decreased gammaglobulin levels result in poor opsonization of infectious agents. The combination of depressed fibronectin and immunoglobulin leads to impaired wound repair and depressed opsonization, both of which encourage colonization of the wound with infectious agents and systemic invasion. As the RES function is also impaired, infectious agents entering the blood are not readily cleared, and sepsis and multiorgan failure ensues. In such patients, replacement therapy with the combination product of the invention is expected to be of great benefit by providing components which act synergistically in wound repair, opsonization, and RES function.

DESCRIPTION OF THE PREFERRED EMBODIMENTS

Figure 1:
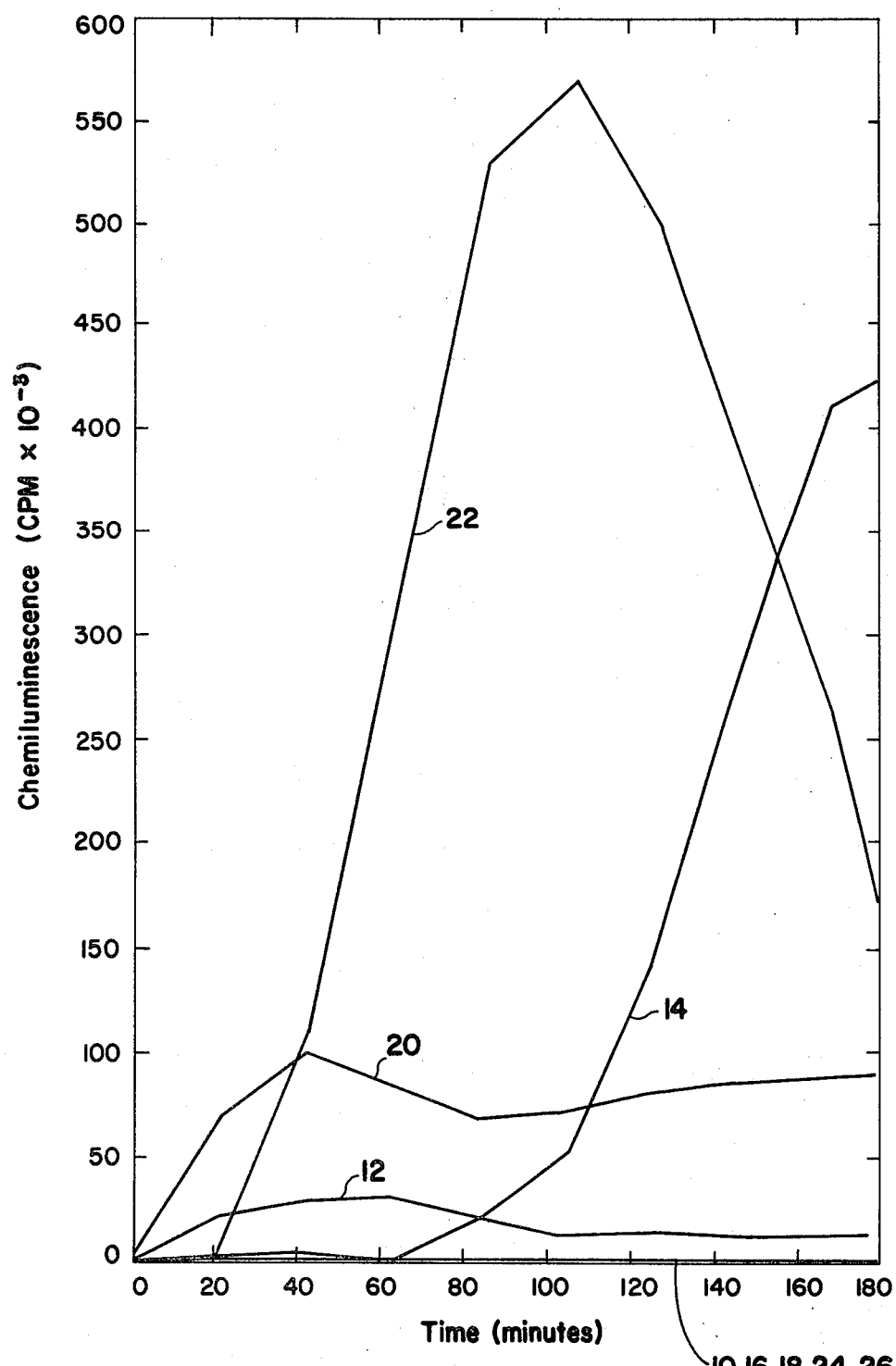
FIG. 1 is a grafh depicting the chemiluminescence of a composition of the invention in the presence of $10^{-6}$ M luminol.

As mentioned above, the composition of the invention comprises a purified immune globulin and purified fibronectin in amounts sufficient to produce an opsonic activity greater than the opsonic activity of the individual agents alone or to produce a phagocytosis of infectious agents (such as particulates, bacteria, immune complexes, viruses, etc.) greater than that of the individual agents alone. Generally, the amount of immune globulin in the composition will be about 0.01–1000 parts per part of fibronectin, preferably about 0.01–500 parts per part of fibronectin, more preferably about 1–100 parts per part of fibronectin.

As the preferred purified immune globulin (IG) one may use material prepared in the same manner in which material intended for intravenous (IVIG) use is prepared. IVIG is well known and can be prepared by known means, such as ultracentrifugation (Barandun et al, Vox Sang., 7, 157–174 [1962]), pH adjustments (Koblet et al, Vox Sang., 13, 93–102 [1967]), careful fractionation (Schneider et al, Vox Sang., 31, 141–151 [1976]), enzymatic modification (Fahey et al, J. Exper. Med., 118, 845–868 [1963]; Kneapler et al, Vox Sang., 32 159–164 [1977]), structural modification (Barandun et al, Monogr. Allergy, 9, 39–60 [1975]), chemical modification (Stephan, Vox Sang., 28, 422–437 [1975]; Masuko et al, Vox Sang., 32, 175–181 [1977]), and reduction and alkylation (Pappenhagen et al, U.S. Pat. No. 3,903,262). Other IVIG products are described in U.S. Pat. Nos. 3,966,906; 4,165,370; 4,168,303; 4,186,192; 4,272,521; 4,276,283; 3,466,368; 3,916,026; 3,928,580; 4,154,819; 4,216,205; 3,607,858; 3,745,155; 3,763,135; 3,808,189; 4,059,571; 4,075,193; 4,082,734; 4,093,606; 4,118,379; 4,124,576; 4,126,605; 4,137,222; 4,160,763; 4,164,495; and 4,256,631.

Other methods of fractionation to yield IG which may be used include polyelectrolyte affinity adsorption, large scale electrophoresis such as disclosed in U.S. Pat. No. 4,246,085, ion exchange adsorption, polyethylene glycol fractionation, and so forth. However, any method which fractionates an immune globulin comprising either IgG, IgM, IgA, IgE, or IgD or subclasses thereof from a human or non-human source may be used in the present invention. Also included in the scope of the invention are therapeutically active fragments of IG such as, for example, Fc, Fd, or Fab fragments. The specific disclosures of all of the above publications and patents are incorporated herein by reference thereto.

Also contemplated are purified IG products manufactured using biotechnology, i.e., monoclonal antibody or recombinant DNA techniques.

A number of methods are disclosed for preparing purified fibronectin—Engvall et al, Int. J. Cancer, Vol. 20, 2 (1977), Molnar et al, Biochemistry, Vol. 18, 3909 (1979), Chen et al, Analytical Biochemistry, Vol. 79, 144–151 (1977), Mossesson et al, J. Biol. Chem., Vol. 245, No. 21, 5728–5736 (1970), Vianto et al, Biochem. J., Vol. 183, 331–337 (1979), U.S. Pat. Nos. 4,210,580 and 4,315,906; and U.S. Ser. No. 127,340. Therapeutically active fragments of fibronectin are also included within the scope of the invention.

Usually the composition of the invention containing purified fibronectin and immune globulin is substantially free of other proteins normally found in plasma, that is, contains 15% or less, preferably 10% or less, of such protein. However, it is possible to incorporate into the composition other proteins such as fibrinogen or Clq in amounts as needed under a particular circumstance.

A preferred product of the invention is a sterile pharmaceutical composition for therapeutic use, which is suitable for intravenous administration. The product may be in lyophilized form to be reconstituted for use by addition of a suitable diluent, or it may be in the form of an aqueous solution.

For reconstitution of a lyophilized product in accordance with this invention one may employ sterile diluent, which may contain materials generally recognized for approximating physiological conditions and/or as required by governmental regulation. In this respect the sterile diluent may contain a buffering agent to obtain a physiologically acceptable pH, sodium chloride, and/or other substances which are physiologically acceptable and/or safe for human use. In general, the material for intravenous injection should conform to regulations established by the Food and Drug Administration, which are available to those in the field. The protein concentration of the product of the invention should be about 0.1–30%, preferably about 1–15%, on a weight to volume basis.

The present pharmaceutical composition may also be in the form of an aqueous solution containing many of the same substances as described above for the reconstitution of a lyophilized product. It is also within the compass of the invention to include stabilizing agents for the immune globulin or fibronectin as required. For instance, the present composition might contain a carbohydrate such as a sugar or sugar alcohol as described in U.S. Pat. Nos. 4,186,192 ('192) or 4,089,944. If necessary, the composition of the invention could contain maltose in accordance with the teaching of '192 (incorporated herein by reference).

It may be preferred to administer a product that is free of infective hepatitis virus. In this respect the composition of the invention, or the fibronectin alone, may be treated to reduce hepatitis infectivity by, for example, pasteurization, i.e., heating at a temperature and for a time, such as about 60° C. or more for a period of about 10 hours or more. To stabilize the proteins in the instant composition to heat, one may use a carbohydrate either alone or in conjunction with an amino acid or other known stabilizing agents. For this purpose one may use as the carbohydrate a mono-, di-, or trisaccharide such as arabinose, glucose, galactose, maltose, fructose, fibose, mannose, rhammose, cusrose, etc., or a sugar alcohol such as sorbitol and mannitol, etc., in an amount of about 0.5–2.4 g/ml of a solution containing 0.1–10% protein.

As mentioned above the products of the invention may be incorporated into pharmaceutical preparations which may be used for therapeutic purposes. However, the term "pharmaceutical preparation" is intended in a broader sense herein to include preparations containing a protein composition in accordance with this invention used not only for therapeutic purposes, but also for reagent or diagnostic purposes as known in the art or for tissue culture. The pharmaceutical preparation intended for therapeutic use should contain a therapeutic amount of fibronectin and immune globulin, i.e., that amount necessary for preventative or curative health measures. If the pharmaceutical preparation is to be employed as a reagent or diagnostic, then it should contain reagent or diagnostic amounts of fibronectin and immune globulin.

EXAMPLES

The invention described above is demonstrated further by the following illustrative examples. The methods employed were modifications of existing procedures.

An established radiolabeled bacterial uptake technique (Allred et al: J. Immunol. Methods, 26: 355–63, 1979), chemiluminescence procedure (Hemming et al: J. Clin. Invest., 58: 1379–87, 1976, and Bryant et al, Immuno-pharmacology, 3: 19–29 1981), and visual microscopic exam method (Hemming et al, ibid) for assessing phagocytic uptake of Group B streptococci were employed. Materials used in these studies included a type III group B streptococcal strain (Rus) which can be opsonized by IVIG, (produced by the methods of U.S. Pat. Nos. 3,903,262 and 4,186,192 which are incorporated herein by reference) and fibronectin (prepared by the method of U.S. Ser. No. 127,340, which is incorporated herein by reference).

All procedures were performed with human phagocytic cells (PMN's) either suspended in liquid medium or after they were attached to gelatin-coated coverslips. Gelatincoated glass coverslips (18×18 mm #1) were prepared by immersion in a 2% solution of warm gelatin (Sigma Chemical Co.). The coverslips were allowed to stand at room temperature for 18 hours prior to use and were used within 48 hours of preparation.

For radiolabeling experiments, bacterial organisms were grown overnight with or without added [$^3$H] thymidine (5 microCuries/ml) in McCoy's Medium, washed and adjusted to $1 \times 10^9$ colony forming units per ml (OD=0.9 at 620 nm). Prior to opsonization, radiolabeled organisms were heat killed at 60° C. for two hours (Allred et al, ibid).

Bacterial organisms were opsonized at 37° C. for 60 minutes with rotation (Allred et al, ibid; Hemming et al, ibid; Bryant et al, ibid) in combinations of fibronectin and IVIG as well as in these preparations alone. The opsonization mixture contained 3 ml of group B streptococci at a concentration of $3.4 \times 10^7$ organisms (colony forming units CFU) per ml, IVIG, fibronectin, or a combination of the two with a total volume brought to 4 ml. The amount of fibronectin alone and in combination with IVIG was 100 and 200 micrograms per milliliter; the IVIG was used in a concentration of 10 mg/ml. The organisms were then washed in PBS and resuspended in medium 199 (Grand Island Biologicals Co.) at a concentration of $2.5 \times 10^7$ ml.

Adult human PMN's were isolated by standard techniques (Allred et al, ibid and Hemming et al, ibid) and used to prepare monolayers on 18 mm×18 mm glass coverslips as described above. As indicated, coverslips were used untreated or treated with 2% gelatin. Nonadhering cells were washed away after 30 minutes incubation and 0.5 ml of the opsonized labeled bacteria were added. At 90 or 180 minute intervals, coverslips were vigorously washed to remove uningested bacteria and placed into scintillation vials containing 6 ml aquasol and counted for ten minutes in a Beckman LS-8000 scintillation counter. Additional studies to differentiate attached from ingested organisms employed cytochalasin-B (Sigma Chemical Co.) in a concentration of 5 micrograms/ml. This agent has been reported to prevent ingestion while not affecting attachment of bacteria to phagocytes (Zurier et al, Proc. Nat'l. Acad. Sci. USA, 70: 844–48, 1973; Malawista et al, Yale J. Biol. Med., 44: 286–300, 1971; Zigmond et al, Exp. Cell Res., 73: 383–39, 1972; Proctor et al, ibid). Stained coverslips were also examined and the number of adherent phagocytic cells per coverslip were determined using an ocular micrometer (Allred et al, ibid). The percentage of organisms ingested was then determined by radioactive counts and by visual assessment of the percentage of PMN's with associated bacteria.

In addition to the radiolabeled uptake experiments, chemiluminescence generation by human PMN's exposed to the preopsonized, live unlabeled bacteria prepared as described above was also assessed. For these studies isolated human PMN's (approximately $5 \times 10^6$) were mixed with 0.5 ml of the preoposonized live bacteria ($1 \times 10^9$/ml) in dark adapted scintillation vials (Hemming et al). The studies were carried out with the cells suspended in a total volume of 3.5 ml of Dulbecco's PBS with CaCl. The vials were placed immediately in the scintillation counter and counted at ten-minute intervals for a total of up to 240 minutes.

The results are summarized in the following tables and in FIG. 1.

TABLE 1

UPTAKE OF RADIOLABELED TYPE III GROUP B STREPTOCOCCI (GBS) OPSONIZED IN IVIG AND FIBRONECTIN (FN)
Percent Radiolabelled Bacterial Uptake*

| Experiment | IVIG$^a$ | FN$^b$ | IVIG + FN |
|---|---|---|---|
| 1 | 44% | 0% | 50.3% |
| 2 | 33% | 0.1% | 71.1% |
| 3 | 33.7% | 3.5% | 48.2% |
| Mean ± SD | 39.6 ± 6.2 | 1.2 ± 2.0 | 56.6 ± 12.6 |

*Background counts subtracted from experimental values.
$^a$IVIG at 10 mg/ml
$^b$FN at 100 micrograms/ml

TABLE 2

OPSONIC ACTIVITY OF IVIG AND FN FOR TYPE III GBS ASSESSED VISUALLY AND BY RADIOLABELED BACTERIAL UPTAKE*

| | Labeled Bacterial Uptake (%) | PMN's with Associated Bacteria (%) |
|---|---|---|
| IVIG$^a$ | 33.8 | 16 |
| FN$^b$ | 3.5 | 6 |
| IVIG + FN | 48.2 | 33 |

$^a$IVIG at 10 mg/ml in opsonic mixture
$^b$FN at 100 micrograms/ml in opsonic mixture
*Background counts subtracted from experimental values.

TABLE 3

PEAK CHEMILUMINESCENCE GENERATED BY PMN's EXPOSED TO IVIG AND FN OPSONIZED TYPE III GBS*

| | Peak CL in C.P.M. × $10^{-3}$ | | |
|---|---|---|---|
| Experiment | IVIG$^a$ | FN$^b$ | IGIV + FN |
| 1 | 1300 | 450 | 2700 |
| 2 | 153 | 44 | 224 |
| 3 | 3060 | 714 | 6290 |

*Background counts subtracted from experimental values.
$^a$IVIG 10 mg/ml
$^b$FN 100 micrograms/ml FIG. 1 graphically depicts chemiluminescence (CPM×$10^{-3}$) in the presence of $10^{-6}$ M luminol of various combinations versus time in minutes. The lines are identified as follows:

| Line | Composition |
|---|---|
| 10 | PMN's alone |
| 12 | PMN's + bacteria |
| 14 | PMN's + FN |
| 16 | PMN's + cytochalasin B (cytoB) |
| 18 | PMN's + cytoB + FN |
| 20 | PMN's + IVIG |
| 22 | PMN's + FN + IVIG |
| 24 | PMN's + IVIG + cytoB |
| 26 | PMN's + IVIG + FN + cytoB |

As can be seen the combination of FN and IVIG resulted in leukocyte chemiluminescence (an indirect measure of phagocytosis) (line 22) greater than the additive chemiluminescence of FN (line 14) and IVIG (line 20) alone. Ingestion not attachment is shown by comparing lines 22 and 24. In the presence of cytoB the combination of FN and IVIG gave a substantially reduced chemiluminescence thus indicating ingestion of bacteria, not mere attachment.

We claim:

1. A pharmaceutical composition comprising purified immune globulin and fibronectin in amounts sufficient to produce an opsonic activity in the composition that is greater than the additive opsonic activity of the immune globulin and fibronectin alone.

2. The composition of claim 1 which is a sterile aqueous solution.

3. The composition of claim 2 wherein the concentration of immune globulin and fibronectin is about 1–30%, weight to volume.

4. The composition of claim 2 wherein the immune globulin is intravenous immune globulin and the concentration of the immune globulin and fibronectin is about 5–15%, weight to volume.

5. The composition of claim 2 wherein the immune globulin is intramuscular immune globulin and the concentration of the immune globulin and fibronectin is about 10–20%, weight to volume.

6. The composition of claim 1 which contains 0.01–1000 parts of immune globulin per part of fibronectin, weight to weight.

7. The composition of claim 6 which contains 0.1–500 parts of immune globulin per part of fibronectin, weight to weight.

8. The composition of claim 7 which contains 1–100 parts of immune globulin part of fibronectin, weight to weight.

9. The composition of claim 1 wherein the immune globulin is immune serum globulin.

10. The composition of claim 9 wherein the immune serum globulin is suitable for intravenous administration.

11. A pharmaceutical composition suitable for intravenous administration for treatment of impaired reticuloendothelial system function and reduced ability for opsonization of infectious agents, which comprises an intravenously injectable purified immune globulin and fibronectin in the ratio of about 0.01–1000 parts of immune globulin per part of fibronectin, on a weight to weight basis.

12. The composition of claim 11 which contains about 0.1–500 parts of immune globulin per part of fibronectin on a weight to weight basis.

13. The composition of claim 11 which contains about 1–100 parts of immune globulin per part of fibronectin, on a weight to weight basis.

14. The composition of claim 11 wherein the combined concentration of immune globulin and fibronectin is about 1–30% in an aqueous medium, on a weight to volume basis.

15. A method of treating a patient having impaired reticuloendothelial system function and reduced ability for opsonization of infectious agents which comprises administering to the patient the composition of claim 11.

16. A pharmaceutical composition comprising purified immune globulin and fibronectin in amounts sufficient to produce a phagocytosis of infectious agents greater than the additive effect from fibronectin and immune globulin alone.

17. The composition of claim 16 which contains about 0.01–1000 parts of immune globulin per part of fibronectin, on a weight to weight basis.

18. The composition of claim 16 wherein the combined concentration of immune globulin and fibronectin is about 1–30% in an aqueous medium, on a weight to volume basis.

19. In a composition comprising an immune globulin, the improvement comprising fibronectin in a synergistic amount.

20. The composition of claim 19 which contains 0.1–500 parts of immune globulin per part of fibronectin.

21. The composition of claim 19 which further includes a carbohydrate.

22. The composition of claim 21 wherein the amount of carbohydrate is about 1–20% by weight.

* * * * *